United States Patent [19]
Matsuo et al.

[11] Patent Number: 5,679,330
[45] Date of Patent: Oct. 21, 1997

[54] SHAMPOO COMPOSITION

[75] Inventors: Takashi Matsuo, Ichikawa; Yasuo Suzuki, Okegawa; Kumiko Yamada, Kisarazu; Kazuyuki Yahagi, Tokyo, all of Japan

[73] Assignee: Kao Corporation, Tokyo, Japan

[21] Appl. No.: 364,991

[22] Filed: Dec. 28, 1994

[30] Foreign Application Priority Data

Dec. 28, 1993 [JP] Japan .................. 5-335779

[51] Int. Cl.$^6$ .................. A61K 7/06; A61K 7/075
[52] U.S. Cl. .................. 424/70.19; 424/70.28; 424/70.11; 424/70.31; 252/DIG. 13
[58] Field of Search .................. 424/70.19, 70.28, 424/70.31, 70.11; 252/DIG. 13

[56] References Cited

U.S. PATENT DOCUMENTS

| | | | |
|---|---|---|---|
| 3,156,656 | 11/1964 | Libby et al. | 424/70.19 |
| 3,980,769 | 9/1976 | Ghilardi et al. | 424/70 |
| 5,078,990 | 1/1992 | Martin et al. | 424/70 |
| 5,318,727 | 6/1994 | Ohtawa | 252/547 |

FOREIGN PATENT DOCUMENTS

| | | |
|---|---|---|
| 0 247 832 | 12/1987 | European Pat. Off. . |
| 472107 | 2/1992 | European Pat. Off. . |
| 0 595 493 | 5/1994 | European Pat. Off. . |

*Primary Examiner*—Salle M. Gardner
*Attorney, Agent, or Firm*—Oblon, Spivak, McClelland, Maier & Neustadt, P.C.

[57] ABSTRACT

A shampoo composition containing the following ingredients (a), (b), (c), and (d):

(a) a nonionic surfactant of an alkylene oxide adduct type,
(b) a compound of a quaternary ammonium salt type, which has an aliphatic chain or which has an ether, an ester, or an acyl compound having an aliphatic chain, and which has a secondary or tertiary amino group and a quaternary ammonium group,
(c) an anionic surfactant, and
(d) a water-soluble polymer.

The shampoo composition produces excellent creamy foams, and fingers smoothly pass through the hair fibers during shampooing and rinsing. The hair after drying is soft, and is handled easily with natural beauty. The dried hair is smoothly combed. Moreover, the composition is mild to the skin and the hair.

13 Claims, No Drawings

SHAMPOO COMPOSITION

BACKGROUND OF THE INVENTION

1. Field of the Invention

The present invention relates to a shampoo composition which is mild to the skin and hair and which has excellent lathering properties, detergency, and excellent conditioning effects.

2. Description of the Related Art

Recently, consumer behavior in connection with hair care has greatly changed, as seen by the increased frequency of shampooing and the preference for long hair. With this trend, shampoos which have enhanced lathering properties, high detergency, which are mild to the hair, and which have excellent conditioning effects have become strongly desired.

To meet this demand, the inventors of the present invention proposed a detergent composition having good hair conditioning properties. The composition contains a compound of a quaternary ammonium salt type, the compound being an acyl compound which has an aliphatic chain, a secondary or tertiary amino group, and a quaternary ammonium group (see Japanese Patent Application Laid-open (kokai) No. 4-149123).

Although that composition has excellent detergency, it still needs improvement in conditioning effects when compared to rinses or similar products.

Accordingly, shampoo compositions which are mild to the hair, which have enhanced lathering properties and high detergency, and which provide conditioning effects comparable to rinses are strongly desired.

Under the above circumstances, the inventors of the present invention carried out extensive studies, and as a result, found that shampoo compositions containing a nonionic surfactant of an alkylene oxide adduct type, a compound of specific quaternary ammonium salt type, an anionic surfactant, and a water-soluble polymer are mild to the skin and the hair, and have high foam-producing ability, high detergency, and excellent rinsing effects, leading to completion of the invention.

SUMMARY OF THE INVENTION

Accordingly, the present invention provides a shampoo composition which comprises the following components (a) to (d):

(a) a nonionic surfactant of an alkylene oxide adduct type, (b) a compound of a quaternary ammonium salt type, which has an aliphatic chain or which has an ether, an ester, or an acyl compound having an aliphatic chain, and which has a secondary or tertiary amino group and a quaternary ammonium group.

(c) an anionic surfactant, and (d) a water-soluble polymer.

Examples of component (a), nonionic surfactants of an alkylene oxide adduct type, which can be used in the present invention include polyoxyalkylene alkyl ethers, polyoxyalkylene alkyl phenyl ethers, polyoxyalkylene aliphatic esters, polyoxyalkylene sorbitan aliphatic esters, polyoxyalkylene aliphatic monoalkanolamides, and polyoxyalkylene aliphatic dialkanolamides. Among these, polyoxyalkylene alkyl ethers and polyoxyalkylene aliphatic monoalkanolamides are preferred, and polyoxyalkylene alkyl ethers are the most preferred. Oxyalkylene groups which are added to these surfactants are C2-C4 oxyalkylene groups, preferable examples of which include oxyethylene and oxypropylene. It is preferred that these groups be added in an amount of 3 to 40 units on average, and particularly preferably from 15 to 25 units on average per hydrophobic residual group such as a long chain alkyl or a long chain acyl. Generally speaking, distributions of the mol number of added molecules are somewhat broad under normal circumstances. However, there is no particular limitation on distribution profiles, and they can be sharp distributions or single variances. Moreover, it is preferred that the carbon number of the long chain alkyl group or the long chain acyl group of the above surfactants be from 6 to 36, and particularly from 8 to 24.

Specific examples of the nonionic surfactants (a) which are particularly preferred include polyoxyethylene lauryl ethers and polyoxyethylene lauric acid monoethanolamides.

Component (a) of the invention may be used singly or in combination of two or more. When the amount of the surfactants is from 1 to 60% by weight, particularly from 2 to 30% by weight, based on the total weight of the shampoo composition, excellent foam producing ability is prominent.

The compounds of a quaternary ammonium salt type, component (b), preferably have the following formula (1):

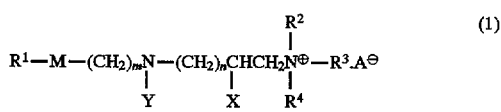

(1)

wherein $R^1$: C7-C35 linear or branched alkyl or alkenyl, $R^2$, $R^3$, $R^4$: the same or different from each other, and represent C1-C4 alkyl or hydroxyalkyl, of hydrogen, M: —CONJ— wherein J represents H, C1-C3 alkyl or hydroxyalkyl; —O—; or —COO—, and Y: H, C1-C36 linear or branched alkyl, alkenyl or hydroxyalkyl, or the following group:

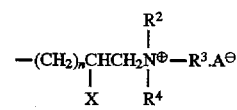

with the proviso that Y is neither C1–C3 alkyl nor C1–C3 hydroxyalkyl in the case where J is C1–C3 alkyl or hydroxyalkyl, X: H or hydroxy, A: a halogen ion, OH, or an organic anion such as a C1–C4 alkyl sulfuric group, m: a number 2 or 3, and n: an integer from 0 to 5, inclusive, with the proviso that X is H or hydroxy when n is equal to 1, and that X is H when n is equal to 0, 2, 3, 4, or 5.

In formula (1), M is preferably —CONJ— and —COO—, with —CONJ— being particularly preferred. In other words, among the compounds of a quaternary ammonium salt type of formula (1), those represented by formula (2) are preferred.

(2)

wherein $R^1$, $R^2$, $R^3$, $R^4$, J, X, A, m, and n have the same meaning as defined hereinabove, and Y' represents H, C1–C3 alkyl or hydroxyalkyl, or the following group:

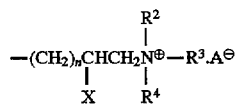

with the proviso that Y is neither C1–C3 alkyl nor C1–C3 hydroxyalkyl in the case where J is C1–C3 alkyl or hydroxyalkyl.

Among the compounds of a quaternary ammonium salt type, component (b), those represented by formula (3) are preferred. They may include the compounds of formula (5) or (6) which are produced as by-products during the process of manufacture.

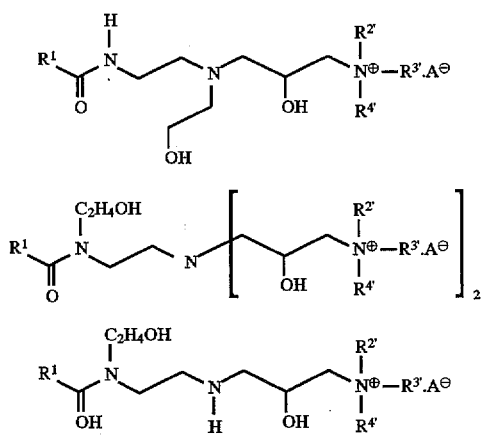

wherein $R^1$ and A have the same meaning as defined above, and $R^{2'}$, $R^{3'}$, and $R^{4'}$ are the same or different from each other, and represent C1–C4 alkyl or hydroxyalkyl.

Of the compounds of a quaternary ammonium salt type represented by formula (3), those in which $R^1$ is C7–C21 and particularly C11–C17 linear or branched alkyl or alkenyl are preferred. In particular, those in which $R^1CO-$ is lauroyl or myristoyl and $R^{2'}$, $R^{3'}$, and $R^4$ are all methyl are more preferred.

The compounds of a quaternary ammonium salt type of formula (3) according to the present invention can be prepared, for example, by the following process.

As shown in flow scheme 1 below, an aliphatic acid ($R^1CO_2H$) and aminoethylethanolamine represented by the following formula (7) are reacted to produce an imidazoline derivative of formula (8) below. The resulting derivative is treated with an alkali, and is converted into a quaternary compound by the reaction with a compound of formula (9). Thus, a compound of a quaternary ammonium salt type represented by formula (3) can be obtained. The obtained compound is preferably purified by desalting it by electrodialysis in view of the solubility and viscosity characteristics of the water-soluble polymers which are contained in the shampoos of the invention.

Flow Scheme 1:

Imidazolination

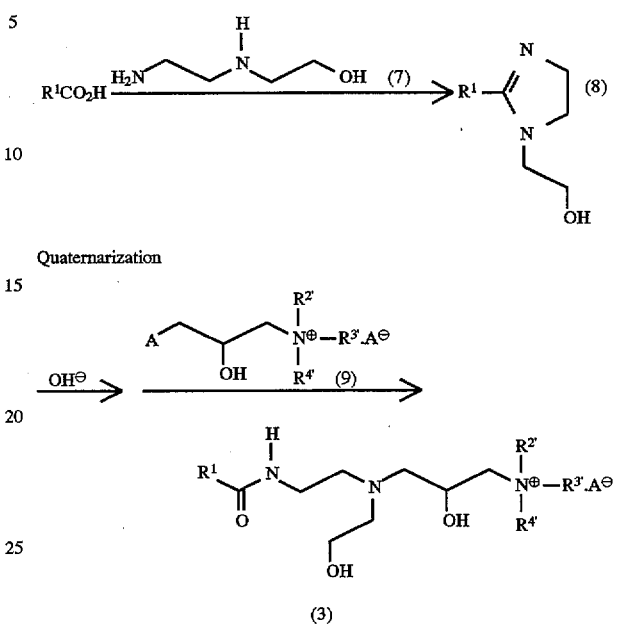

wherein $R^1$, $R^{2'}$, $R^{3'}$, $R^{4'}$, and A have the same meaning as defined above.

Another preferable group of the compounds of a quaternary ammonium salt type, component (b), are those represented by the following formula (4):

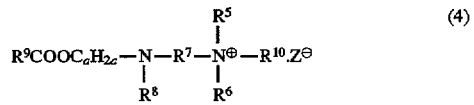

wherein $R^5$ and $R^6$ are the same or different from each other, and represent C1–C4 alkyl, $R^7$ represents C2–C6 alkylene or alkenylene, $R^8$ represents C4–C36, preferably C8–C36 linear or branched alkyl or alkenyl, $R^9$ represents C7–C35 linear or branched alkyl or alkenyl, $R^{10}$ represents hydrogen, or C1–C4 alkyl or hydroxyalkyl, Z represents halogen, sulfate, bisulfate, carboxylate which may be substituted by a C1–C4 hydroxyl group, or C1–C4 alkylsulfate, and a represents an integer from 2 to 9.

Among these compounds of formula (4), those in which $R^5$ and $R^6$ are methyl, $R^7$ is C2–C3 alkylene, $R^8$ is hydrogenated beef tallow alkyl or hydrogenated palm oil alkyl, and $R^9CO$ is hydrogenated beef tallow aliphatic acyl or hydrogenated palm oil aliphatic acyl are more preferred.

The compounds of a quaternary ammonium salt type, compounds of formula (4), which are used in the present invention can be prepared, for example, by the following process.

As shown in flow scheme 2 below, if an ester amine of formula (10) is reacted with an acidic substance or a quaternarizing agent of formula (11), a compound of a quaternary ammonium salt type of formula (4) can be obtained.

Flow Scheme 2:

$$R^9COOC_aH_{2a}-\underset{\underset{R^8}{|}}{N}-R^7-N\begin{matrix}R^5\\ \diagup\\ \diagdown\\ R^6\end{matrix} + R^{10}Z \longrightarrow$$

(10)                    (11)

$$R^9COOC_aH_{2a}-\underset{\underset{R^8}{|}}{N}-R^7-\underset{\underset{R^6}{|}}{N^\oplus}-R^{10}.Z^\ominus$$

(4)

wherein $R^5$, $R^6$, $R^7$, $R^8$, $R^9$, $R^{10}$, Z, and a have the same meaning as defined above.

Component (b) of the invention may be used singly or in combination of two or more. When the amount of components (b) is from 1 to 20% by weight, particularly from 2 to 10% by weight, based on the total weight of the shampoo composition, excellent conditioning effects can be obtained, and in particular, softness and smoothness of the hair during rinsing are prominent.

Examples of the anionic surfactants, component (c), which are used in the present invention include the following (i) to (xi) surfactants.

(i) Alkylbenzene sulfonates (in particular, linear or branched alkylbenzene sulfonates having an alkyl group containing 10 to 16 carbon atoms on average are preferred).

(ii) Alkyl or alkenyl ether sulfates of an alkylene oxide adduct type (particularly preferred are those having a linear or branched alkyl or alkenyl containing 10 to 20 carbon atoms on average, in which 0.5 to 8 moles on average of ethylene oxide, propylene oxide or butylene oxide are added, per 1 molecule of sulfate, with the ratio of ethylene oxide/propylene oxide being 0.1/9.9 to 9.9/0.1 or with the ratio of ethylene oxide/butylene oxide being 0.1/9.9 to 9.9/0.1).

(iii) Alkyl or alkenyl sulfates (in particular, those having alkyl or alkenyl containing 10 to 20 carbon atoms on average are preferred).

(iv) Olefin sulfonates (in particular, those containing 10 to 20 carbon atoms on average per molecule are preferred).

(v) Alkane sulfonates (in particular, those containing 10 to 20 carbon atoms on average per molecule are preferred).

(vi) Saturated or unsaturated fatty acid salts (in particular, those containing 10 to 24 carbon atoms on average per molecule are preferred).

(vii) Aliphatic salts of an alkylene oxide adduct type (particularly preferred are alkyl or alkenyl ether carboxylates having an alkyl or alkenyl group containing 10 to 20 carbon atoms on average, in which 0.5 to 8 moles on average of ethylene oxide, propylene oxide or butylene oxide are added, per 1 molecule of carboxylate, with the ratio of ethylene oxide/propylene oxide being 0.1/9.9 to 9.9/0.1 or with the ratio of ethylene oxide/butylene oxide being 0.1/9.9 to 9.9/0.1).

(viii) Alpha-sulfofatty acid salts or esters (in particular, those having alkyl or alkenyl containing 10 to 20 carbon atoms on average per molecule are preferred).

(ix) N-acylamino acid-type surfactants (in particular, those having a C8 to C24 acyl group or a free carboxylic acid residue are preferred).

(x) Phosphoric acid mono- or di- ester-type surfactants (in particular, those having a C8 to C24 alkyl or alkenyl group are preferred).

(xi) Sulfosuccinic esters (in particular, those derived from a higher aliphatic amide, or those of a C8 to C22 higher alcohol or its ethoxylates are preferred).

Examples of the counter ions of the anionic residues of these anionic surfactants include alkali metal ions such as a sodium ion, a potassium ion, etc.; alkaline earth metal ions such as a calcium ion, a magnesium ion, etc.; an ammonium ion; and alkanol amines containing 1 to 3 alkanol groups having 2 to 3 carbon atoms (such as monoethanolamine, diethanolamine, triethanolamine and triisopropanolamine).

Among the above anionic surfactants, those listed below are particularly preferred: (2) alkyl ether sulfates, (3) alkyl sulfates, (6) saturated or unsaturated fatty acid salts, (9) acylated amino acids, (10) surfactants of phosphoric monoester type, and (11) sulfosuccinic esters. Specific examples of particularly preferred ones are sodium polyoxyethylene laurylether sulfates (2 to 3 moles on average of ethylene oxide have been added), laurylsulfuric acid triethanolamines, sodium salts of coconut oil fatty acids, coconut oil aliphatic amide ether sulfates, lauroyl-N-methyltaurines, lauroyl-N-methyl-beta-alanines, disodium N-myristoyl-L-glutamates, lauroyl-beta-alanines, disodium polyoxyethylene laurylsulfosuccinates (3 to 7 E.O.), laurylphosphoric acids, N-lauroyl-N'-carboxymethyl-N'-(2-hydroxyethyl)ethylenediaminetriethanolamine salts, and N-lauroyl-N-(2-hydroxyethyl)-N',N'-bis(carboxymethyl)-ethylenediamine sodium salts.

These anionic surfactants, which are component (c), are used singly or in combination of two or more. When they are used in a proportion from 1 to 20% by weight, preferably from 3 to 15% by weight, based on the total weight of the composition, excellent lathering ability and high conditioning effects are obtained.

Component (d), water-soluble polymers, which can be used in the present invention may be naturally occurred, semi-synthetic, or synthetic polymers. Moreover, any one of cationic polymers, anionic polymers, nonionic polymers can be used.

Examples of naturally-occurred water-soluble polymers include vegetable polymers such as gum arabic, tragacanth gum, galactan, guar gum, carob gum, caraya gum, carrageenan, pectin, agar, quince seeds (*Cydonia oblonga*), and glycyrrhizic acid; microorganism-derived polymers such as xanthane gum, dextran, succinoglucan, and pullulan; and protein hydrolysate polymers such as keratin decomposition derivatives, etc.

Examples of semi-synthetic water-soluble polymers include starch polymers such as cationic starch, carboxymethyl starch, and methylhydroxypropyl starch; cellulose polymers such as cationic cellulose derivatives, methylcellulose, nitrocellulose, ethylcelluloce, methylhydroxypropylcellulose, hydroxyethylcellulose, sodium cellulose sulfate, hydroxypropylcellulose, carboxymethylcellulose-Na (CMC), crystalline cellulose, and cellulose powders; alginate polymers such as sodium alginate and propylene glycol alginate; and cationic guar gum derivatives.

Examples of synthetic water-soluble polymers include homopolymers of diallyl quaternary ammonium salts; copolymers of diallyl quaternary ammonium salt/acrylic amide; quaternarized polyvinylpyrrolidone derivatives; polyvinylpyrrolidones; copolymers of vinylpyrrolidone and vinyl acetate, alkylaminoacrylate, etc.; lower alkyl half esters of a copolymer of methylvinyl ether and maleic anhydride, copolymers of vinyl acetate and crotonic acid, etc.; copolymers of acrylic acid and/or methacrylic acid and an acrylic alkyl ester and/or a methacrylic alkyl ester; copolymers of acrylic acid, acrylic alkyl ester, and N-alkylacrylic amide; amphoteric copolymers of dialkylaminoethyl methacrylate, dialkylaminoethyl acrylate, diactone acrylic amide, etc. and acrylic acid, methacrylic acid, acrylic alkyl ester, methacrylic alkyl ester, etc.; tertiary copolymers of acrylic hydroxypropyl, methacrylic butylaminoethyl, and acrylic octylamide; and copolymers of alkyl acrylamide, acrylate, alkylaminoalkyl acrylamide, and polyethylene glycol methacrylate.

Among the above water-soluble polymers, particularly preferred are those containing an amino group or an ammonium group as linked to a polymer chain, or containing dimethyldiallylammonium halide as a monomer unit. Specific examples include homopolymers of diallyl quaternary ammonium salts, cationic cellulose derivatives, cationic starches, cationic guar gum derivatives, copolymers of diallyl quaternary ammonium salt/acrylic amide, and quaternary polyvinyl pyrrolidone derivatives.

Examples of the cationic cellulose derivatives which are preferred include those of formula (12):

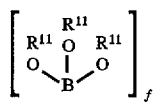
(12)

wherein B represents a residue of an unhydroglucose unit, f represents an integer from 50 to 20,000, and $R^{11}$ represents the substituent of formula (13):

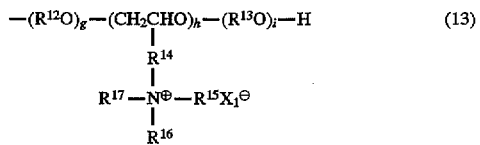
(13)

wherein $R^{12}$ and $R^{13}$ each independently represent C2–C3 alkylene, g is an integer from 0 to 10, h is an integer from 0 to 3, i is an integer from 0 to 10, $R^{14}$ is C1–C3 alkylene or hydroxyalkylene, $R^{15}$, $R^{16}$, and $R^{17}$ are the same or different from each other and represent aryl or aralkyl which may form a heterocyclic ring containing a nitrogen atom in the formula, and $X_1$ represents an anion such as a chlorine ion, a bromine ion, an iodine ion, a sulfuric ion, a sulfonic ion, a methylsulfuric ion, a phosphoric ion, a nitric ion, etc.

The cationic substitution degree of these cationic cellulose derivatives, or the average number of h per unit unhydroglucose is preferably 0.01 to 1, and more preferably 0.02 to 0.5. The sum of g and i is 1 to 3 on average. Cationic substitution degrees of less than 0.01 are just insufficient. Whereas, although the cationic substitution degree may exceed 1, degrees not more than 1 are particularly preferred in view of the yield of the reaction. Preferable molecular weight of the cationic cellulose derivative is in the range from 100,000 to 3,000,000.

Preferable cationic cellulose starches are those represented by formula (14):

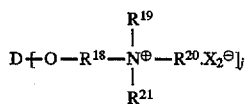
(14)

wherein D represents a starch residue, $R^{18}$ represents C1–C10 alkylene or hydroxyalkylene, $R^{19}$, $R^{20}$, and $R^{21}$ are the same or different from each other and represent alkyl, aryl, or aralkyl which have carbon atoms of 10 or less and which may form a heterocyclic ring containing a nitrogen atom in the formula, and $X_2$ represents an anion such as a chlorine ion, a bromine ion, an iodine ion, a sulfuric ion, a sulfonic ion, a methylsulfuric ion, a phosphoric ion, a nitric ion, etc.

The cationic substitution degree of these cationic starches, or the number of cationic group introduced per unit of anhydrous glucose, is preferably from 0.01 to 1, and more preferably from 0.02 to 0.5. Cationic substitution degrees of less than 0.01 are just insufficient. Whereas, although the cationic substitution degree may exceed 1, degrees not more than 1 are particularly preferred in view of the yield of the reaction.

Preferable cationic guar gum derivatives are those represented by formula (15):

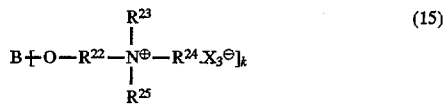
(15)

wherein E represents a guar gum residue, $R^{22}$ represents C1–C10 alkylene or hydroxyalkylene, $R^{23}$, $R^{24}$, and $R^{25}$ are the same or different from each other and represent alkyl, aryl, or aralkyl which have carbon atoms of 10 or less and which may form a heterocyclic ring containing a nitrogen atom in the formula, and $X_3$ represents an anion such as a chlorine ion, a bromine ion, an iodine ion, a sulfuric ion, a sulfonic ion, a methylsulfuric ion, a phosphoric ion, a nitric ion, etc., and k represents a positive integer.

The cationic substitution degree of these cationic guar gum derivatives is preferably from 0.01 to 1. Especially, those in which 0.02 to 0.5 cation groups are introduced into a saccharide unit are preferred. Such cationic polymers are described, for example, in Japanese Patent Application publication (kokoku) No. 58-35640, Japanese Patent Application publication (kokoku) No. 60-46158, and Japanese Patent Application Laid-open (kokai) No. 58-53996. They are commercially available under the trademark "JAGUAL" (Cellanese Schtein Hall Co.).

Preferable examples of the cationic diallyl quaternary ammonium salt/acrylic amide copolymers include those represented by the following formula (16) or (17):

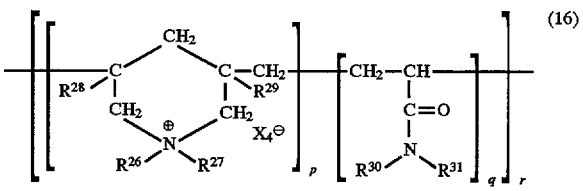
(16)

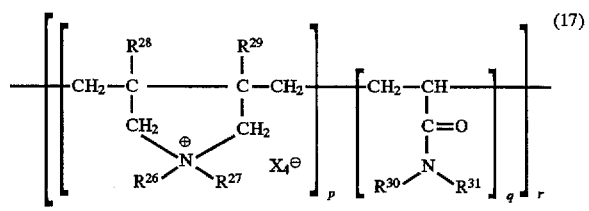
(17)

wherein $R^{26}$ and $R^{27}$ are the same or different from each other and represent hydrogen, alkyl (C1–C18), phenyl, aryl, hydroxy alkyl, amide alkyl, cyano alkyl, alkoxy alkyl, or carboalkoxy alkyl, $R^{28}$, $R^{29}$, $R^{30}$, and $R^{31}$ are the same or different from each other and represent hydrogen, lower alkyl (C1–C3), or phenyl, and $X_4$ represents an anion such as a chlorine ion, a bromine ion, an iodine ion, a sulfuric ion, a sulfonic ion, a methylsulfuric ion, a nitric ion, etc., p represents an integer from 1 to 50, q represents an integer from 0 to 50, and r represents an integer from 150 to 8,000.

The molecular weight of these diallyl quaternary ammonium salt/acrylic amide copolymers and diallyl quaternary ammonium salt homopolymers is preferably from about 30,000 to 2,000,000 and particularly preferably from 100,000 to 1,000,000.

Examples of the quaternarized polyvinyl pyrrolidone derivatives which are preferred include those represented by the following formula (18):

$$\left(CH-CH_2\right)_s\left(CH_2-\underset{\underset{C}{|}}{\overset{\overset{R^{32}}{|}}{C}}\right)_t \quad (18)$$

with side groups: $H_2C{-}N{-}C{=}O$, $H_2C{-}CH_2$ and $O{-}Y_1{+}CH_2{\frac{}{u}}\overset{\oplus}{N}{\underset{R^{35}}{\overset{R^{33}}{\underset{|}{-}R^{34}}}}\ X_5^{\ominus}$ wherein $R^{32}$ represents hydrogen or C1–C3 alkyl, $R^{33}$, $R^{34}$, and $R^{35}$ are the same or different from each other and represent hydrogen, C1–C4 alkyl, hydroxy alkyl, amide alkyl, cyano alkyl, alkoxy alkyl, or carboalkoxy alkyl, $Y_1$ represents oxygen or a group NH in an amide bond, $X_5$ represents an anion such as a chlorine ion, a bromine ion, an iodine ion, a sulfuric ion, a sulfonic ion, an alkyl sulfuric ion having 1 to 4 carbon atoms, phosphoric ion, and nitric ion, etc., u represents an integer from 1 to 10, and s and t are integers making the sum, s+t, from 20 to 8,000.

The molecular weight of these quaternarized polyvinylpyrrolidone derivative is preferably from 10,000 to 2,000,000 and particularly preferably from 50,000 to 1,500,000.

These water-soluble polymers, component (d), can be used singly or in combination of two or more. When they are incorporated in an amount from 0.01 to 3% by weight, preferably from 0.3 to 1.5% by weight, based on the total weight of the shampoo compositions of the present invention, excellent rinsing effects can be obtained.

The shampoo compositions of the present invention may further contain, besides the above-described essential components, other optional components which are ordinarily used in the manufacture of cosmetics, medicines, and foods. Such optional components include pharmaceutical agents such as anti-dandruffs typified by zinc pyrrithione (Zpt), germicides, and vitamins; preservatives such as parabene; humectants such as propylene glycol, glycerol, diethylene glycol monoethyl ether, sorbitol, pantenol, and glycinebetaine; coloring agents such as dyes and pigments; conditioning agents such as perfluoro polyethers; pearl-hue imparting agents such as glycol esters; chitosan derivatives such as hydroxypropyl chitosan; blended perfumes of various kinds; and other ingredients described in "ENCYCLOPEDIA OF SHAMPOO INGREDIENTS" (Micelle Press, 1985) as long as they do not impede the effects of the present invention.

The shampoo compositions of the present invention produce excellent creamy foams. During shampooing and rinsing, fingers smoothly comb the hair. The hair after drying gives soft feel to the touch, and has natural beauty when it is styled. Combs smoothly pass through the dried hair fibers. In addition, the compositions are mild to the skin and the hair, and irritation is suppressed. Accordingly, they are especially useful as shampoo compositions.

EXAMPLES

The present invention will next be described by way of examples, which should not be construed as limiting the invention.

Example 1

The shampoo compositions (invention products 1 to 3 and comparative products 1 to 7) shown in Table 1 were prepared, and their performance was evaluated according to the following criteria. The foam-producing ability was evaluated using a reversal stirring method. Fuel to the touch of the hair was evaluated in the following manner. 1 g of shampoo was applied to 20 g (15 cm long) of hair fibers of healthy Japanese women, and lathered for 1 minute. Thereafter, the hair fibers were rinsed with water, toweldried, and then dried with a dryer. This procedure was carried out by 5 expert panelists, who made evaluation.

The results are shown in Table 1.

Evaluation Criteria

Foam-producing Ability

A: excellent latherability

B: good latherability

C: insufficient latherability

D: foam was hardly produced

Feel to the Touch of Hair

A: soft and smooth touch, with remarkably smooth finger-combing

B: smooth touch with smooth finger-combing

C: fingers cannot smoothly comb the hair fibers

D: rough touch to the hair, causing entangled hair fibers

Finger-combing During Rinsing

A: feels no braking, with remarkably smooth finger-combing

B: feels slight braking with smooth finger-combing

C: feels braking with difficulty in finger-combing

D: feels considerable braking, with very poor finger-combing

Softness of the Hair after Towel-drying:

A: very soft and resilient

B: soft

C: lack of softness

D: rough

Handling of the Hair After Dried with a Dryer

A: very easily handled as desired

B: handled without particular difficulty

C: slightly poor handling

D: poor handling with hair fibers springing out

Easiness of Combing After the Hair is Dried with a Dryer

A: smooth and excellent combing

B: slight catching

C: catching especially at the tip of the hair fibers

Mildness to the Skin

A: no irritation–slight irritation

B: weak irritation

C: medium–strong irritation

TABLE 1

|  | Products of Invention | | | Comparative Products | | | | | | |
| --- | --- | --- | --- | --- | --- | --- | --- | --- | --- | --- |
|  | 1 | 2 | 3 | 1 | 2 | 3 | 4 | 5 | 6 | 7 |
| Compositions (wt. %): | | | | | | | | | | |
| Polyoxyethylene(16)lauryl ether | 10 | 10 | 10 |  |  |  | 16 | 10 | 10 |  |
| (Myristoyl-N-hydroxyethyl)aminoethyl-2-hydroxypropyl trimethyl ammonium*¹ | 4 | 6 | 6 | 16 |  |  |  |  |  | 6 |
| Polyoxyethylene(3)laurylsulfate.Na | 6 |  |  |  | 16 |  |  |  |  |  |
| Polyoxyethylene(3)laurylsulfo-succinate.Na |  | 4 |  |  |  | 16 |  | 6 |  | 4 |
| N-myristoyl-L-glutamic acid.2Na |  |  | 4 |  |  |  |  |  | 6 |  |
| Cationic polymer 1*² | 0.5 |  |  | 0.3 | 0.5 |  | 0.3 |  |  |  |
| Cationic polymer 2*³ |  | 0.5 | 0.3 |  |  | 0.5 |  | 0.5 | 0.5 | 0.5 |
| Purified water |  | balance |  |  |  | balance |  |  |  |  |
| Results of evaluation: | | | | | | | | | | |
| Latherability | A | A | A | A | A | B | C | B | C | D |
| Feel to the touch of the hair during shampooing | B | B | B | B | B | C | D | C | C | A |
| Smoothness of finger combing during rinsing | A | A | A | B | C | B | D | C | C | A |
| Softness of hair after towel-drying | A | A | A | C | C | B | D | D | C | A |
| Easy handling after drying | A | A | A | C | C | B | D | D | C | A |
| Smooth combing after drying | B | B | B | C | C | C | D | D | D | B |
| Mildness to the skin | B | B | B | B | D | B | B | B | B | B |

Note) *¹

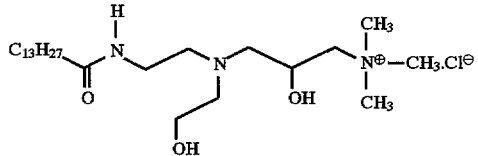

*²Polymer JR-400 (cationic cellulose, product of Union Carbide)
*³Merquat 100 (poly-N,N-dimethyl-3,5-methylenepiperidinium chloride, product of Merck)

Example 2

A shampoo composition having the following formulation was prepared in a conventional manner. This shampoo product had excellent foam-producing ability, and was very mild. During shampooing and rinsing, fingers passed through the hair fibers smoothly. Moreover, the hair after drying was soft, and was handled easily with natural beauty. The dried hair was smoothly combed.

| (Formulation) | wt % |
| --- | --- |
| Polyoxyethylene(16)laurylether | 18 |
| Laurylamine oxide | 3 |
| Compound of a quaternary ammonium salt type*¹ | 5 |
| Sodium polyoxyethylene(3)laurylsulfosuccinate | 5 |
| Cationic polymer*³ | 0.5 |
| Sodium benzoate | 0.3 |
| Colorant | suitable amount |
| Perfume | suitable amount |
| Citric acid | suitable amount |
| Purified water | balance |

*¹:Same as that described in Example 1.
*³:Same as that described in Example 1.

Example 3

A shampoo composition having the following formulation was prepared in a conventional manner. This shampoo product had excellent foam-producing ability, and was very mild. During shampooing and rinsing, fingers passed through the hair fibers smoothly. Moreover, the hair after drying was soft, and was handled easily with natural beauty. The dried hair was smoothly combed.

| (Formulation) | wt % |
| --- | --- |
| Monolauric polyethylene(20)glycol | 5 |
| Polyoxyethylene(18)laurylether | 12 |
| Lauroyl diethanol amide | 3 |
| Compound of a quaternary ammonium salt type*¹ | 4 |
| Sodium acylglutamate*⁴ | 6 |
| High molecular weight dimethylpolysiloxane aqueous emulsion | 1.0 |
| Cationic polymer*⁵ | 0.5 |
| Sodium benzoate | 0.3 |
| Colorant | suitable amount |
| Perfume | suitable amount |
| Citric acid | suitable amount |
| Water | balance |

*¹:Same as that described in Example 1.
*⁴:Amisoft LT-12 (product of Ajinomoto).
*⁵:Caticello H-60 (cationic cellulose, product of Kao)

What is claimed:

1. A shampoo comprising the following ingredients (a), (b), (c), and (d):

(a) 1–60% by weight of a nonionic surfactant selected from the group consisting of polyoxyalkylene alkyl ethers, polyoxyalkylene alkyl phenyl ethers, polyoxyalkylene aliphatic esters, polyoxyalkylene sorbitan aliphatic esters, polyoxyalkylene aliphatic monoalkanolamides, polyoxyalkylene aliphatic dialkanolamides, and mixtures thereof, (b) 1–20% by weight of a compound of a quaternary ammonium salt compound represented by the formula (1):

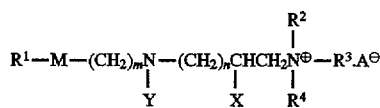

wherein R¹: C7–C35 linear or branched alkyl or alkenyl, R², R³, R⁴: the same or different from each other, and represent C1–C4 alkyl or hydroxyalkyl, or hydrogen, M: —CONJ— wherein J represents H, C1–C3 alkyl or hydroxyalkyl; —O—; or —COO—, and Y: H, C1–C36 linear or branched alkyl, alkenyl or hydroxyalkyl, or the following group:

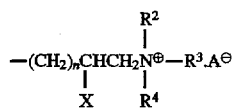

with the proviso that Y is neither C1–C3 alkyl nor C1–C3 hydroxyalkyl in the case where J is C1–C3 alkyl or hydroxyalkyl, X: H or hydroxy, A: a halogen ion or an organic anion, m: a number 2 or 3, and n: an integer from 0 to 5, inclusive, with the proviso that X is H or hydroxy when n is equal to 1, and that X is H when n is equal to 1, 2, 3, 4, or 5;

(c) 1–20% by weight of an anionic surfactant, and (d) 0.1–3% by weight of a water-soluble polymer.

2. The shampoo composition according to claim 1, wherein the component (a) is a polyoxyalkylene alkyl ether.

3. The shampoo composition according to claim 1, wherein the component (b) is a compound represented by the formula (2):

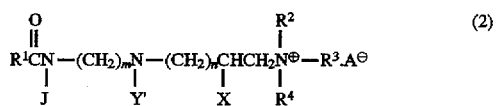

wherein R¹: C7–C35 linear or branched alkyl or alkenyl,

R², R³, R⁴: the same or different from each other, and represent C1–C4 alkyl or hydroxyalkyl, or hydrogen, J: H, C1–C3 alkyl or hydroxyalkyl, Y': H, C1–C3 alkyl or hydroxyalkyl, or the following group:

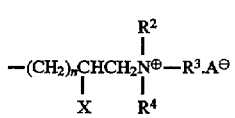

with the proviso that Y' is neither C1–C3 alkyl nor C1–C3 hydroxyalkyl in the case where J is C1–C3 alkyl or hydroxyalkyl, X: H or hydroxy, A: a halogen ion or an organic anion, m: a number 2 or 3, and n: an integer from 0 to 5, inclusive, with the proviso that X is H or hydroxy when n is equal to 1, and that X is H when n is equal to 0, 2, 3, 4, or 5.

4. The shampoo composition according to claim 1, wherein the component (b) is a compound represented by the formula (3):

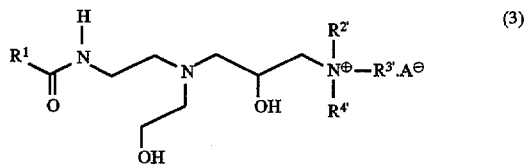

wherein R¹ is C7–C35 linear or branched alkyl or alkenyl, R²', R³', and R⁴' are the same or different from each other, and represent C1–C4 alkyl or hydroxyalkyl, and A is a halogen ion or an organic anion.

5. The shampoo composition according to claim 1, wherein the component (b) is a compound represented by the formula (4):

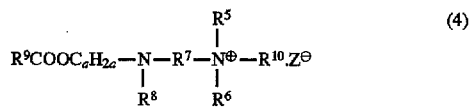

wherein R⁵ and R⁶ are the same or different from each other, and represent C1–C4 alkyl, R⁷ represents C2–C6 alkylene or alkenylene, R⁸ represents C4–C36 branched alkyl or alkenyl, R⁹ represents C7–C35 linear or branched alkyl or alkenyl, R¹⁰ represents hydrogen, or C1–C4 alkyl or hydroxyalkyl, Z represents halogen, sulfate, bisulfate, carboxylate which may be substituted by a C1–C4 hydroxyl group, or C1–C4 alkylsulfate, and a represents an integer from 2 to 9.

6. The shampoo composition according to claim 5, wherein, in the compound of formula (4), R⁵ and R⁶ represent methyl, R⁷ represents C2–C3 alkylene, R⁸ represents hydrogenated beef tallow alkyl or hydrogenated palm oil alkyl, R⁹CO represents hydrogenated beef tallow aliphatic acyl or hydrogenated palm oil aliphatic acyl.

7. The shampoo composition according to claim 1, wherein component (d) is a water-soluble cationic polymer.

8. The shampoo composition as claimed in claim 1, wherein component (b) is (myristoyl-N-hydroxyethyl)aminoethyl-2-hydroxypropyl trimethyl ammonium chloride.

9. The shampoo composition as claimed in claim 4, wherein R¹ in formula (3) is a C₁₁–C₁₇ linear or branched alkyl or alkenyl group.

10. The shampoo composition according to claim 1, wherein component (a) is selected from the group consisting of polyoxyalkylene alkyl ethers, polyoxyalkylene alkyl phenyl ethers, polyoxyalkylene aliphatic esters, polyoxyalkylene sorbitan aliphatic esters, polyoxyalkylene aliphatic monoalkanolamides and polyoxyalkylene aliphatic dialkanolamines, component (b) is a compound represented by the formula (3):

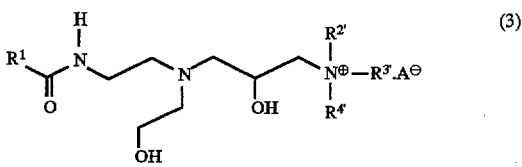

wherein R¹ is a C₇–C₃₅ linear or branched alkyl or alkenyl, R²', R³' and R⁴' are the same or different from each other, and represent C₁–C₄ alkyl or hydroxyalkyl, and A is a halogen ion or an organic anion, component (c) is selected from the group consisting of alkylbenzene sulfonates, alkyl or alkenyl ether sulfate adducts of alkylene oxide, alkyl or alkenyl sulfates, olefin sulfonates, alkane sulfonates, saturated or unsaturated fatty acid salts, aliphatic salts of an alkylene oxide adduct, α-sulfofatty acid salts or esters, N-acylamino acid surfactants, phosphoric acid mono- or di- ester surfactants and sulfosuccinic esters, and component (d) is selected from the group consisting of naturally occurring, semi-synthetic or synthetic water-soluble polymers.

11. The shampoo composition as claimed in claim 10, wherein component (c) is a sulfosuccinic ester.

12. The shampoo composition as claimed in claim 10, wherein component (d) is a homopolymer of diallyl quaternary ammonium salts.

13. The shampoo composition as claimed in claim 1, wherein said anionic surfactant is selected from the group consisting of alkylbenzene sulfonates, alkylene oxide adducts of alkyl or alkenyl ether sulfates, alkyl or alkenyl sulfates, olefin sulfonates, alkane sulfonates, saturated or unsaturated fatty acid salts, aliphatic salts of alkylene oxide adducts, alpha-sulfofatty acid salts or esters, N-acylamino acid surfactants, phosphoric acid mono- or di-ester surfactants and sulfosuccinic esters.

* * * * *